United States Patent
Uthgenannt

(10) Patent No.: US 10,485,553 B2
(45) Date of Patent: Nov. 26, 2019

(54) KNEE RESECTION AND GAP BALANCING INSTRUMENTS AND TECHNIQUES

(71) Applicant: Biomet Manufacturing, LLC, Warsaw, IN (US)

(72) Inventor: Brian A. Uthgenannt, Cricklade (GB)

(73) Assignee: Biomet Manufacturing, LLC, Warsaw, IN (US)

( * ) Notice: Subject to any disclaimer, the term of this patent is extended or adjusted under 35 U.S.C. 154(b) by 237 days.

(21) Appl. No.: 15/717,536

(22) Filed: Sep. 27, 2017

(65) Prior Publication Data
US 2018/0085134 A1    Mar. 29, 2018

Related U.S. Application Data

(60) Provisional application No. 62/401,564, filed on Sep. 29, 2016.

(51) Int. Cl.
*A61B 17/15*  (2006.01)
*A61B 17/02*  (2006.01)
(Continued)

(52) U.S. Cl.
CPC .......... *A61B 17/154* (2013.01); *A61B 17/025* (2013.01); *A61B 17/1285* (2013.01);
(Continued)

(58) Field of Classification Search
CPC ............... A61B 17/154; A61B 17/155; A61B 2017/0268; A61B 17/025
See application file for complete search history.

(56) References Cited

U.S. PATENT DOCUMENTS 4,457,307 A * 7/1984 Stillwell .............. A61B 17/154
                                                         606/178
5,474,559 A * 12/1995 Bertin .................. A61B 17/154
                                                         606/86 R
(Continued)

FOREIGN PATENT DOCUMENTS

EP        0809969       12/1997
WO     2018064183       4/2018

OTHER PUBLICATIONS

"Oxford Partial Knee Microplasty Instrumentation Surgical Technique", (2013), 56 pgs.
(Continued)

*Primary Examiner* — Christian A Sevilla
(74) *Attorney, Agent, or Firm* — Schwegman Lundberg & Woessner, P.A.

(57) ABSTRACT

Methods, systems and apparatuses including apparatuses that can be used in knee replacement procedures are disclosed. According to one example, a method is disclosed that can include determining a desired flexion space between a tibia and a femur with the patient's knee joint oriented in flexion, referencing a tibia resection guide along the tibia a distance from the desired flexion space, resecting a proximal end portion of the tibia with the tibia resection guide, inserting an intramedullary rod into the femur with the patient's knee joint in flexion, tensioning the patient's knee joint to create a flexion gap by separating the tibia and the femur, sequent to tensioning the patient's knee joint, reorienting the femur into extension relative to the tibia and re-tensioning the patient's knee joint to create an extension gap that substantially matches the flexion gap.

18 Claims, 10 Drawing Sheets

(51) Int. Cl.
  *A61B 17/17* (2006.01)
  *A61B 17/88* (2006.01)
  *A61B 17/128* (2006.01)
  *A61B 90/00* (2016.01)
  *A61B 17/56* (2006.01)
  *A61B 17/90* (2006.01)
  *A61B 17/72* (2006.01)
  *A61B 17/00* (2006.01)

(52) U.S. Cl.
  CPC .......... *A61B 17/155* (2013.01); *A61B 17/157* (2013.01); *A61B 17/1764* (2013.01); *A61B 17/8869* (2013.01); *A61B 17/72* (2013.01); *A61B 2017/00115* (2013.01); *A61B 2017/00243* (2013.01); *A61B 2017/00305* (2013.01); *A61B 2017/00314* (2013.01); *A61B 2017/00318* (2013.01); *A61B 2017/00535* (2013.01); *A61B 2017/00734* (2013.01); *A61B 2017/0268* (2013.01); *A61B 2017/564* (2013.01); *A61B 2017/90* (2013.01); *A61B 2090/064* (2016.02); *A61B 2090/065* (2016.02)

(56) References Cited

U.S. PATENT DOCUMENTS

| 2005/0143746 | A1* | 6/2005 | Steffensmeier | A61B 17/154 606/88 |
| 2006/0089653 | A1* | 4/2006 | Auger | A61B 17/155 606/88 |
| 2006/0184173 | A1* | 8/2006 | Collazo | A61B 17/155 606/62 |
| 2007/0173854 | A1 | 7/2007 | Berger et al. | |
| 2009/0043310 | A1 | 2/2009 | Rasmussen | |
| 2015/0045801 | A1 | 2/2015 | Axelson, Jr. et al. | |

OTHER PUBLICATIONS

"Zimmer eLIBRA Neo Classic Balancing System Surgical Technique", (Jul. 22, 2015), 16 pgs.
"Zimmer FuZion Instruments Surgical Technique (Beta Version)", (Oct. 6, 2014), 52 pgs.
"International Application Serial No. PCT/US2017/053752, International Search Report dated Nov. 21, 2017", 5 pgs.
"International Application Serial No. PCT/US2017/053752, Written Opinion dated Nov. 21, 2017", 8 pgs.

* cited by examiner

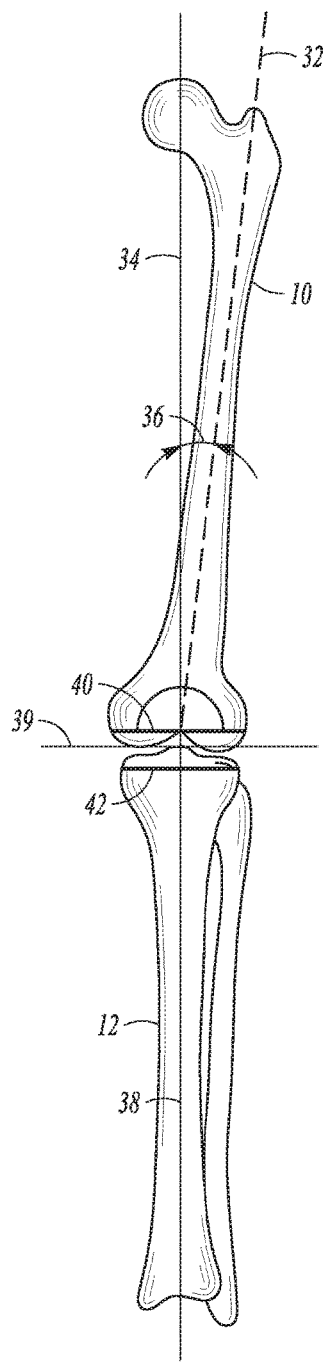
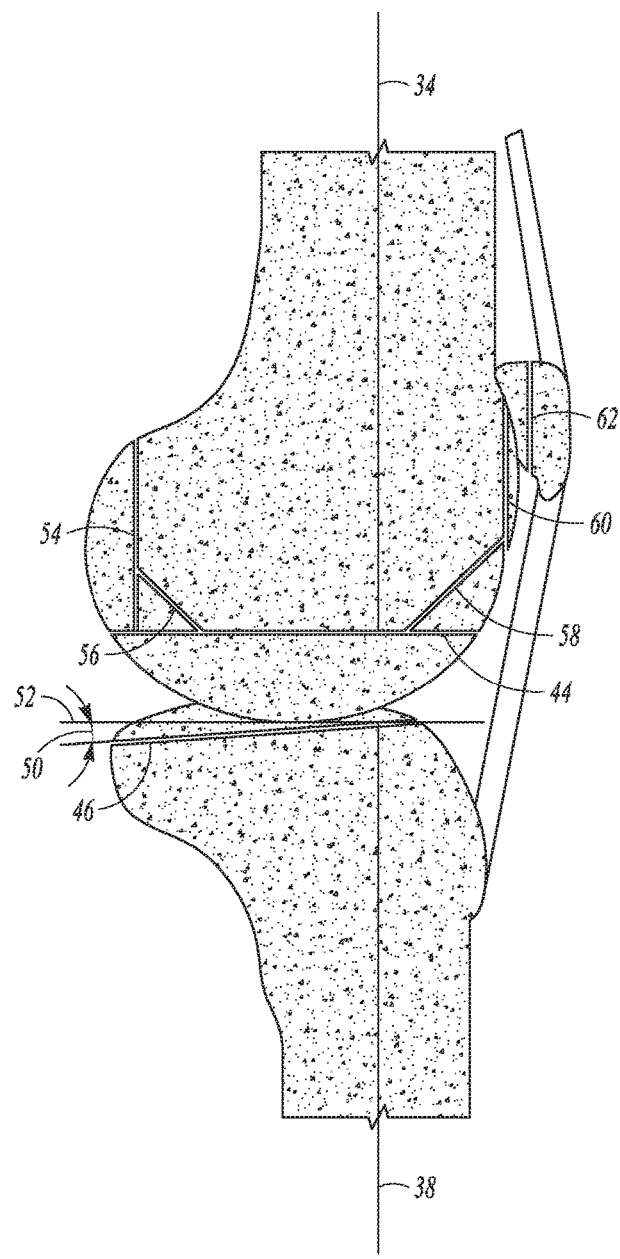
FIG. 1
FIG. 2

KNEE RESECTION AND GAP BALANCING INSTRUMENTS AND TECHNIQUES

CLAIM OF PRIORITY

This application claims the benefit of U.S. Provisional Patent Application Ser. No. 62/401,564, filed on Sep. 29, 2016, the benefit of priority of which is claimed hereby, and which is incorporated by reference herein in its entirety.

FIELD

The present subject matter relates to orthopedic procedures and, more particularly, to bone resection and gap balancing apparatuses and methods for performing knee arthroplasties.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones comprising the joint. Cut guides are used to guide the removal of the articular surfaces that are to be replaced. Prostheses are used to replicate the articular surfaces. Knee prostheses can include a femoral component implanted on the distal end of the femur, which articulates with a tibial component implanted on the proximal end of a tibia to replicate the function of a healthy natural knee. Prior to the knee prostheses being selected and implanted, range of motion and other testing can be performed using trial components and other instruments to insure proper prosthesis size and knee joint kinematics. For example, knee balancing can performed to achieve tension of the ligaments using a knee tensor or balancer.

Overview

The present inventor has recognized, among other things, an opportunity for reducing surgical complexity and providing patients with other benefits. More particularly, the present inventor have recognized that a flexion first surgical technique along with components configured to facilitate such technique can allow the surgeon to restore the medial posterior condylar offset of the femur, size the femur with a reduced possibility of notching and match an extension gap to a flexion gap without having to reduce the patella and/or without having to make preliminary cuts that may require re-cuts to the femur. For example, the present technique and components can allow for minor adjustments to flexion of a femoral component to allow the posterior offset to be maintained while reducing or eliminating anterior femoral notching. Furthermore, the present inventor has recognized that surgical complexity can be reduced as the disclosed flexion first techniques and components can maintain the medial femoral joint-line.

To further illustrate the apparatuses, systems and methods disclosed herein, the following non-limiting examples are provided:

Example 1 is a system for use in a knee arthroplasty of a patient's knee joint, the knee joint including a tibia and a femur, the system can comprise a first assembly, a second assembly and a third assembly. The first assembly can include an insert configured to be disposed between the tibia and the femur with the femur oriented in flexion, the insert can be configured to be contacted by a posterior portion of a condyle of the femur. The first assembly can include a tibial resection guide configured to interface with a posterior portion of the tibia and configured to be disposed from the insert a predefined distance. The second assembly can include an intramedullary rod configured to insert into the femur with the femur in flexion and a tool configured to mount to the intramedullary rod. The tool can include a tibial component configured for placement against the tibia and a femoral component configured for placement against the femur. The femoral component can be moveably coupled to the tibial component to place the patient's knee joint in tension to create a flexion gap by separating the tibia and the femur. The third assembly can include a femoral resection guide configured to define distal resection plane along the femur with the femur in extension. The third assembly can be configured to reference the femoral resection guide from a resected proximal surface of the tibia with the patient's knee joint in extension. The third assembly can include one or more shims configured to be disposed between the tibia and femur to place the patient's knee joint in tension to create an extension gap that substantially matches the flexion gap.

In Example 2, the subject matter of Example 1 optionally includes the tool has a slot extending one or both of generally anterior-posterior and proximal-distal and configured to receive the intramedullary rod therein.

In Example 3, the subject matter of any one or more of Examples 1-2 optionally can further include a stylus configured to couple to the tool and reference an anterior cortex of the femur to determine a size of the femur.

In Example 4, the subject matter of any one or more of Examples 1-3 optionally include the tool defines one or more apertures configured to define a drill path into the distal femur.

In Example 5, the subject matter of any one or more of Examples 1-4 optionally include one or both of the insert and the one or more shims include one or more sensors configured to sense a pressure applied on the one or both of the insert and the one or more shims by one or both of the femur and tibia.

In Example 6, the subject matter of any one or more of Examples 1-5 optionally include the one or more shims are contacted by a member that is inserted in the patient's knee joint, the member is configured to simulated posterior portion of a condyle of the femur.

Example 7 is a method of performing a knee arthroplasty on a patient's knee joint, the method can include determining a desired flexion space between a tibia and a femur with the patient's knee joint oriented in flexion, referencing a tibia resection guide along the tibia a distance from the desired flexion space, resecting a proximal end portion of the tibia with the tibia resection guide, inserting an intramedullary rod into the femur with the patient's knee joint in flexion, tensioning the patient's knee joint to create a flexion gap by separating the tibia and the femur, sequent to tensioning the patient's knee joint, reorienting the femur into extension relative to the tibia, and re-tensioning the patient's knee joint to create an extension gap that substantially matches the flexion gap.

In Example 8, the subject matter of Example 7 optionally includes referencing a femoral resection guide relative to a resected proximal surface of the tibia with the femur in extension.

In Example 9, the subject matter of any one or more of Examples 7-8 optionally can further include sizing the femur sequent to reorienting the femur into the extension orientation.

In Example 10, the subject matter of any one or more of Examples 7-9 optionally can further include sensing a pressure between the tibia and the femur with the patient's knee joint oriented in both extension and flexion.

In Example 11, the subject matter of any one or more of Examples 7-10 optionally include tensioning the patient's knee joint to create a flexion gap by separating the tibia and the femur comprises: coupling a tool to the intramedullary rod, the tool including a tibial component configured for placement against the tibia and a femoral component configured for placement against the femur; and moving the femoral component relative to the tibial component to place the patient's knee joint in tension to create a flexion gap by separating the tibia and the femur.

Example 12 is a method of performing a knee arthroplasty on a patient's knee joint, the method can include positioning an insert between a tibia and a femur with the patient's knee joint oriented in flexion, referencing a tibia resection guide along the tibia a distance from the insert, resecting a proximal end portion of the tibia with the tibia resection guide, inserting an intramedullary rod into the femur with the patient's knee joint in flexion, coupling a tool to the intramedullary rod, the tool including a tibial component configured for placement against the tibia and a femoral component configured for placement against the femur, moving the femoral component relative to the tibial component to place the patient's knee joint in tension to create a flexion gap by separating the tibia and the femur, sequent to coupling the tool and moving the femoral component relative to the tibial component, reorienting the femur into an extension orientation relative to the tibia; and inserting at least one shim between the tibia and femur to place the patient's knee joint in tension to create an extension gap that substantially matches the flexion gap.

In Example 13, the subject matter of Example 12 optionally includes attaching a moveable stylus to the tool, the stylus having a tip configured for contact with an anterior surface of the femur at or adjacent an anterior cortex of the femur.

In Example 14, the subject matter of any one or more of Examples 12-13 optionally further includes repositioning the tool anterior/posterior to move the femoral component relative to a femoral condyle of the femur.

In Example 15, the subject matter of Example 14 optionally includes adjusting flexion of the knee with the tool coupled to the intramedullary rod and the femur.

In Example 16, the subject matter of any one or more of Examples 12-15 optionally can further include providing one or more holes in the tool that define one or more drill paths into the femur.

In Example 17, the subject matter of Example 16 optionally includes inserting a drill through at least one of the one or more holes in the tool, operating the drill to form one or more apertures in the femur, attaching a cut guide to the one or more apertures in the femur, and performing a posterior femoral resection of the femur utilizing the cut guide.

In Example 18, the subject matter of any one or more of Examples 12-17 optionally can further include sensing a pressure applied on one or both of the insert and the at least one shim.

In Example 19, the subject matter of any one or more of Examples 12-18 optionally can further include contacting the at least one shim against a simulated posterior portion of a condyle of the femur.

In Example 20, the apparatuses, system and/or method of any one or any combination of Examples 1-19 can optionally be configured such that all elements or options recited are available to use or select from.

These and other examples and features of the present apparatuses and methods will be set forth in part in the following Detailed Description. This Overview is intended to provide non-limiting examples of the present subject matter—it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

FIG. 1 is a front elevation view of a tibia and a femur showing axes of the knee joint according to example of the present application.

FIG. 2 is a side section view of a knee joint showing typical bone cuts used in replacing the joint surfaces according to example of the present application.

DETAILED DESCRIPTION

The present application relates to devices, systems and methods that can be used in a knee replacement procedure, such as a total knee replacement procedure, as well as other types of knee replacement procedures. The present application discloses various assemblies that can be used together as a system for accomplishing portions of the knee replacement procedure. The system can include a first assembly that is configured to check a flexion space within the knee joint. The first assembly can also be configured to establish a tibial resection based upon such flexion space. According to some examples, the system can include a second assembly that can include a tool mountable to an intramedullary rod. The second assembly can be configured to establish a flexion gap. According to further examples, the second assembly can be configured to determine a femoral size. The system can include a third assembly that can be configured to match an extension gap to the flexion gap.

Figure 3:
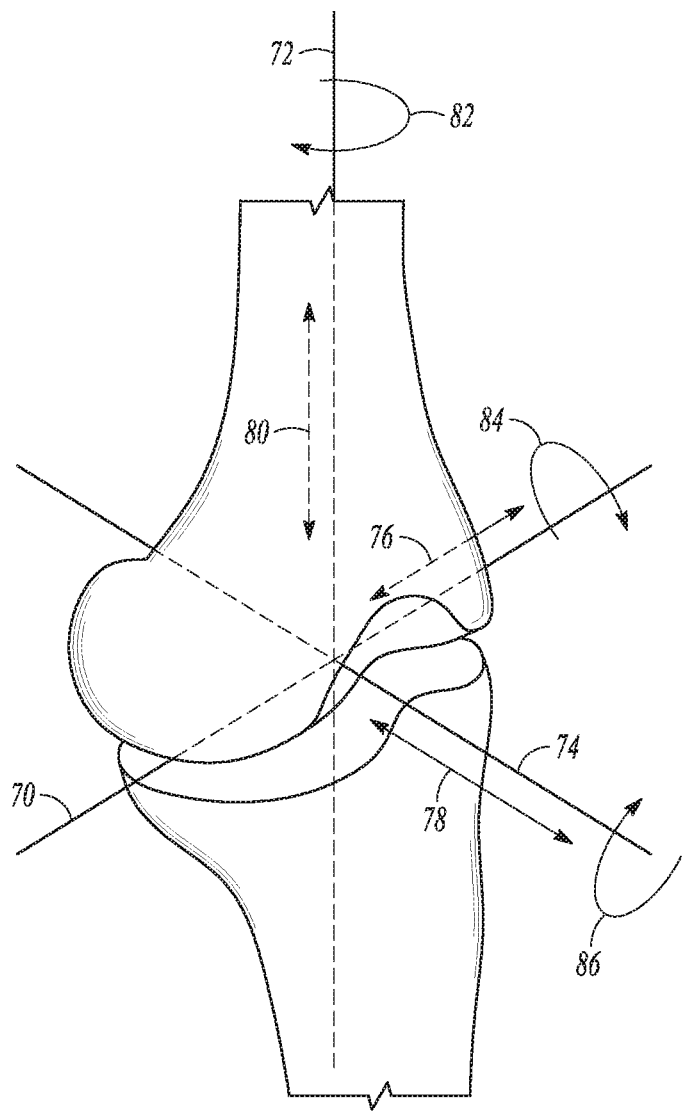
FIG. 3 is a perspective view of knee joint showing aspects of component positioning according to example of the present application.

FIGS. 1-3 illustrate several aspects relevant for system and assembly as well as implant orientation. FIG. 1 illustrates various axes of the lower limb in the frontal plane. Axes can be defined for each segment of the lower limb. For example, the femur 10 has an anatomic axis 32 coinciding generally with its intramedullary canal. It also has a mechanical axis 34, or load axis, running from the center of the femoral head to the center of the knee. The angle 36 between these two axes 32, 34 in the frontal plane varies within the patient population but is on the order of 4-9°. The two axes 32, 34 are approximately superimposed in the sagittal plane (FIG. 2). Likewise, the tibia 12 has a mechanical axis 38 coinciding generally with its intramedullary canal. The mechanical axis 38 of the tibia 12 runs from the center of the knee to the center of the ankle. The transverse axis, or joint line 38, about which the knee flexes, is parallel to a line through the medial and lateral femoral condyles and parallel to the tibial plateau. Typically, the distal femur and proximal tibia are resected to be parallel to the joint line 39, and thus perpendicular to the mechanical axes 34, 38 as indicated at 40 and 42. The intersection of the femoral and tibial mechanical axes 34, 38 may subtend a small angle relative to one another. However, the angle can be small such that the axes 34, 38 are approximately collinear and may be treated as collinear for most purposes.

FIG. 2 illustrates the knee joint from the side or sagittal view and various bone cuts that may be made to align implant components. The distal femoral cut 44 is typically made perpendicular to the femoral axes 32, 34 in the sagittal plane. The proximal tibial resection 46 is typically cut to match the natural posterior slope, or rotation, of the proximal tibia relative to the mechanical axes 34, 38. The amount of posterior to anterior slope 50 relative to a reference line 52 perpendicular to the mechanical axes 34, 38 varies in the patient population but is on the order of 5° to 7°. The distance between the distal femoral cut 44 and proximal tibial cut 46 along the mechanical axes 34, 38 is the extension gap. Other cuts may be made depending on the components that are to be implanted. These include a posterior femoral cut 54, posterior femoral chamfer cut 56, anterior femoral chamfer cut 58 and anterior femoral cut 60. The patella 62 may also be cut to allow for replacement of the patellar articular surface.

FIG. 3 depicts six aspects of component positioning relative to a coordinate system in which the x-axis 70 corresponds approximately to the joint line 39, the z-axis 72 corresponds approximately to the mechanical axes 34 and 38, and the y-axis 74 is normal to the other two. Position along each of these axes is depicted by arrows. Position along the x, y, and z axes determines the medial/lateral (dx) 76, anterior/posterior (dy) 78, and proximal/distal (dz) 80 positioning of components respectively. Rotation about each of these axes is also depicted by arrows. Rotation about the z-axis (rz) 82 corresponds anatomically to external rotation of the femoral component, rotation about the x-axis (rx) 84 corresponds to extension plane rotation, and rotation about the y-axis (ry) 86 corresponds to varus/valgus rotation.

FIG. 4A-6B show a system 100 that can be used for a knee arthroplasty of a knee joint 102 of a patient. Prior to the examples of FIGS. 4A-6B, one or more incisions can be made to access the knee joint 102. In some cases, osteophytes and/or ligaments can be removed from knee joint 102, for example. The knee joint 102 can include the tibia 12 and the femur 10 as previously discussed.

Figure 4A:
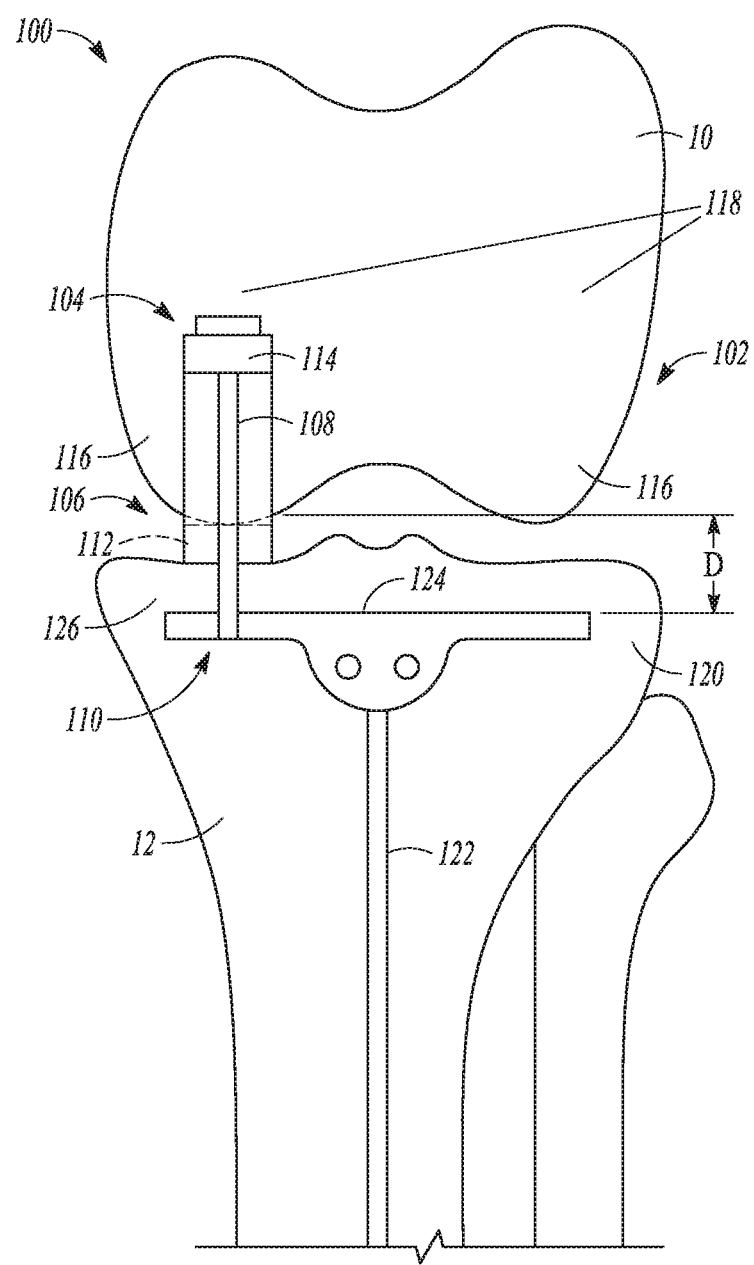
FIG. 4A is a plan view of a knee joint of a patient in a coronal plane having a first assembly positioned therein and adjacent thereto according to an example of the present application.
Figure 4B:
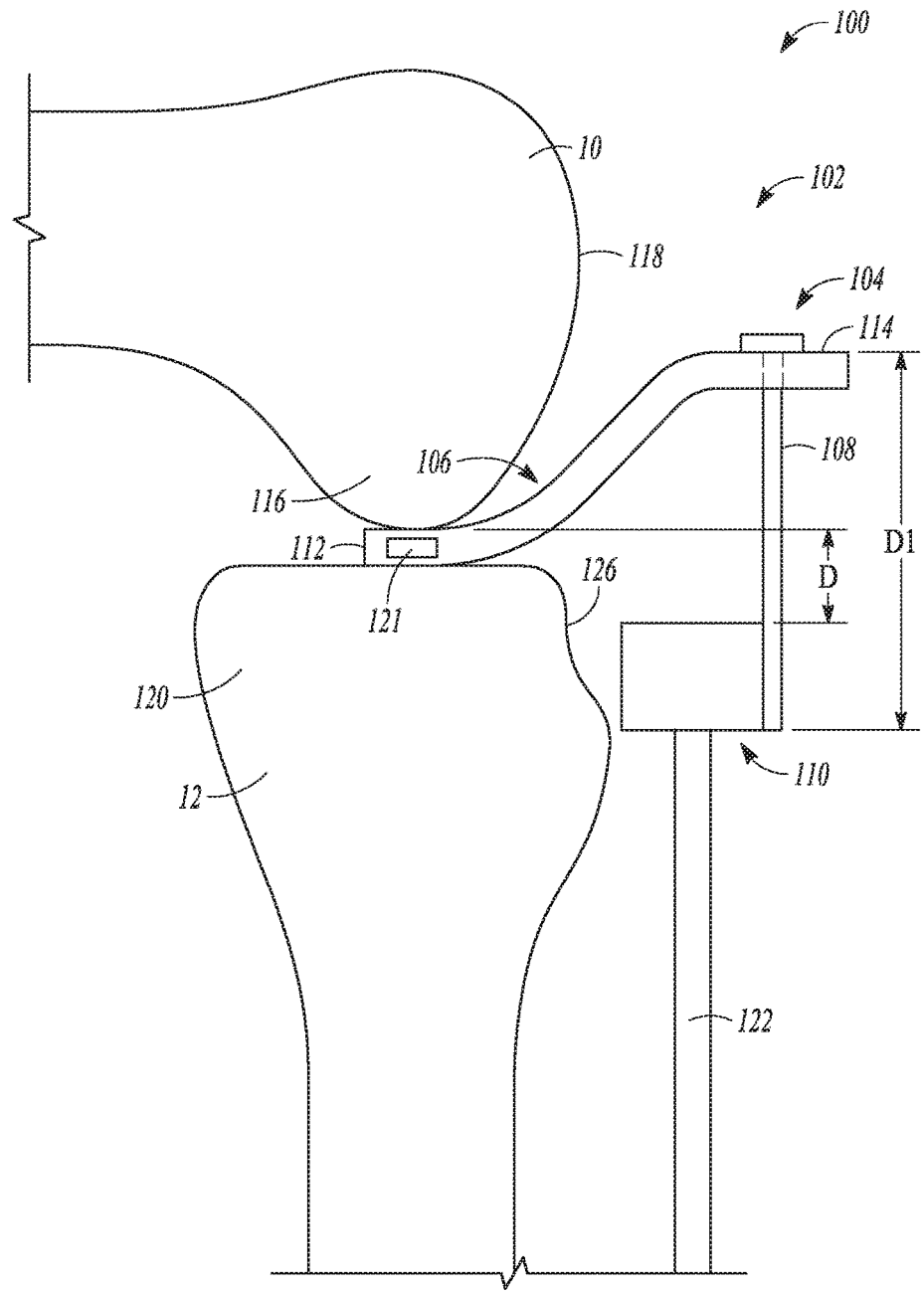
FIG. 4B is a plan view of the knee joint and the first assembly of FIG. 4A in a sagittal plane according to example of the present application.

The example of FIGS. 4A and 4B show a first assembly 104. In particular, FIG. 4A shows an example of the first assembly 104 in a coronal plane and FIG. 4B shows the first assembly 104 in a sagittal plane. As shown in the example of FIGS. 4A and 4B, the first assembly 104 can include an insert 106, a coupling 108 (only shown in FIG. 4B) and a tibial resection guide 110. The insert 106 can include a finger portion 112 and an extension 114.

The insert 106 can be configured to be disposed between the tibia 12 and the femur 10 with the femur 10 oriented in flexion as shown in FIGS. 4A and 4B. The insert 106, in particular the finger portion 112, can be configured to be contacted by a posterior portion 116 of a condyle 118 of the femur. In some examples, the finger portion 112 can be configured to size the femur 10 based upon the contact with the posterior portion 116 of the condyle 118. The finger portion 112 can also house one or more sensors 121 as shown in FIG. 4B. The one or more sensors 121 can be configured to sense a pressure applied on the finger portion 112 by one or both of the femur 10 and tibia 12. The sensed pressure can be used to determine the amount of resection/balance desirable for the posterior portion 116 of the condyle 118. The extension 114 can extend generally anteriorly from the finger portion 112 to connect to the coupling 108. The coupling 108 can comprise a clamp and a rod and can couple the insert 106 to the tibial resection guide 110. The coupling 108 can extend a predefined proximal-distal distance D1 (e.g., 9 mm) from the insert 106 to the tibial resection guide 110, for example.

The tibial resection guide 110 can be configured to assist in performing a resection of a proximal portion 120 of the tibia 12. The tibial resection guide 110 can be mounted to the tibia 12, for example by use of a rod 122 that is coupled to an ankle of the patient. According to further examples, the tibial resection guide 110 can be mounted using other means such as with bone screws or via the coupling 108.

According to the example of FIGS. 4A and 4B, the tibial resection guide 110 can have a resection feature 124 (FIG. 4A) such as a slot or planar surface configured to assist in guiding resection of the proximal portion 120 of the tibia 12. The tibial resection guide 110 can be configured to interface with a posterior portion 126 of the tibia 12 and can be configured to couple to the insert 106 via the coupling 108 as previously discussed. Thus, the tibial resection guide 110 can be disposed the predefined distance D from a surface of the insert 106 that contacts the femur. Once a desired position of the tibial resection guide 110 is achieved resection of the proximal portion 120 of the tibia 12 can be performed.

Figure 5A:
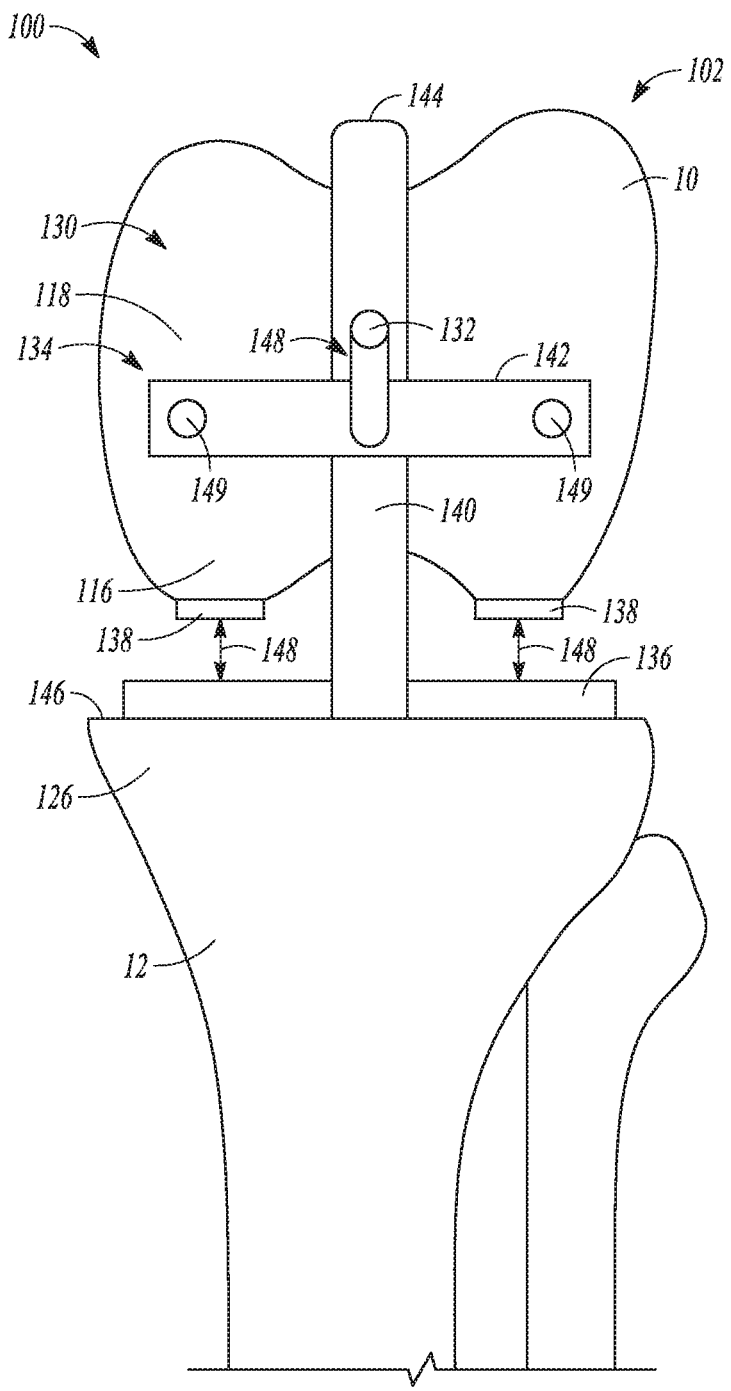
FIG. 5A is a plan view of the knee joint of the patient in the coronal plane having a second assembly positioned therein and adjacent thereto according to an example of the present application.
Figure 5B:
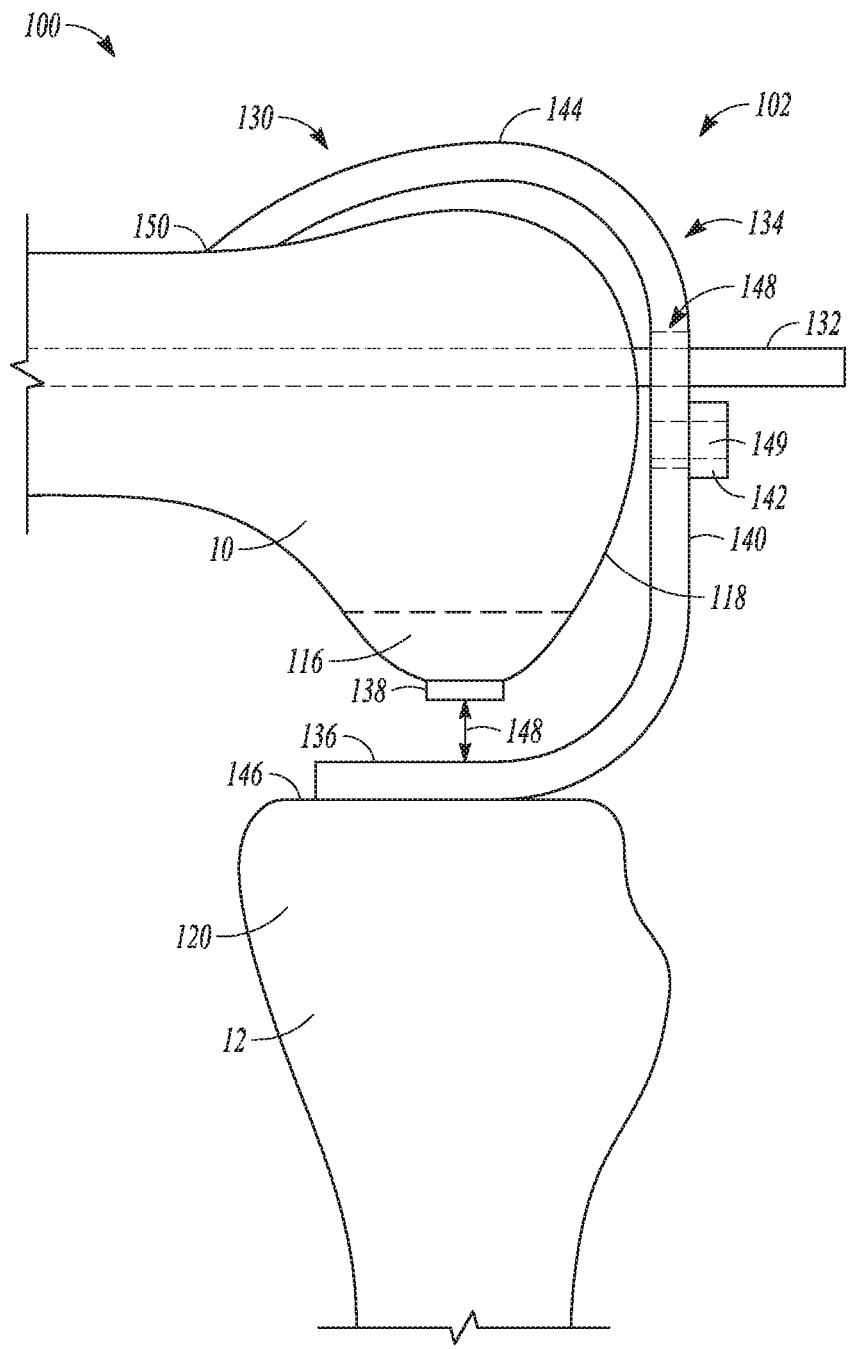
FIG. 5B is a plan view of the knee joint and the second assembly of FIG. 5A in a sagittal plane according to example of the present application.

FIGS. 5A and 5B show an example of a second assembly 130 that can be part of the system 100. In particular, FIG. 5A shows an example of the second assembly 130 in a coronal plane and FIG. 5B shows the second assembly 130 in a sagittal plane. As shown in the example of FIGS. 5A and 5B, the second assembly 130 can include an intramedullary rod 132 and a tool 134. The tool 134 can include a tibial component 136, a femoral component 138, a main body 140, a cross-member 142 (FIG. 5A only) and a stylus 144.

As shown in FIGS. 5A and 5B, the intramedullary rod 132 can be configured to insert into the femur 10 with the femur 10 in flexion. The tool 134 can be configured to mount to the intramedullary rod 132. The tibial component 136 can be configured for placement against the tibia 12 (i.e. can be configured to be placed against a resected proximal surface 146 of the tibia 12) and the femoral component 138 can be configured for placement against the femur 10 (e.g., against the posterior portion 116 of the condyle 118). According to the example of FIGS. 5A and 5B, the femoral component 138 can be moveably coupled to the tibial component 136 to place the patient's knee joint 102 in tension to create a flexion gap 148 by separating the tibia 12 and the femur 10. As shown in FIG. 5A, the flexion gap 148 for the medial condyle can differ from the flexion gap for the lateral condyle. As used herein the flexion gap 148 can refer to either the gap of the medial condyle or the lateral condyle. The flexion gap 148 can be selected based upon performance of various kinematic tests on the knee joint, surgeon feel, achieving a desired degree of tension of the ligament(s) and/or other soft tissue, for example.

The main body 140 can extend generally proximal-distal and can connect to the tibia component 136, the femoral component 138, the cross-member 142 and the stylus 144. The tibial component 136 can be shaped as a paddle or plate according to one example. The femoral component 138 can be shaped as a paddle to engage with one or more of the condyles. The cross-member 142 can extend generally medial-lateral and can define one or more aperture 149 configured to define a drill path into the distal femur 10. In some examples, the one or more apertures 149 can be used fixate the tool 134 to the femur 10. The one or more apertures 149 can additionally or alternatively be used to form one or more holes in the femur 10 that can be used to mount a femoral cut guide (not shown) such as a 4-in-1 femoral cut guide to the femur 10.

According to some examples, the tool 134, in particular the main body 140, can have a slot 148 that can extend generally anterior-posterior and/or proximal-distal along the main body 140. The slot 148 can be configured to receive the intramedullary rod 132 therein as shown in FIGS. 5A and 5B. The slot 148 can be configured to facilitate repositioning the tool 134, for example, by allowing anterior-posterior and/or proximal-distal movement of the tool 134 relative to the femur 10 and the intramedullary rod 132 to reposition the femoral component 138 relative to the condyle 118 of the femur 10. Additionally, the slot 148 can be configured to allow for adjustment of the flexion of the knee joint 102 with the tool 134 remaining coupled to the intramedullary rod 132 and the femur 10.

The stylus 144 can extend anterior-posterior and proximal-distal from the main body 140 and can be configured to reference an anterior cortex 150 (FIG. 5B only) (e.g., contact the anterior portion of the femur at or adjacent the anterior cortex 150) of the femur 10 to determine a size of the femur 10. According to the example of FIGS. 5A and 5B, an anterior, distal portion of the stylus 144 can couple to the tool 134 at the main body 140.

Figure 6A:
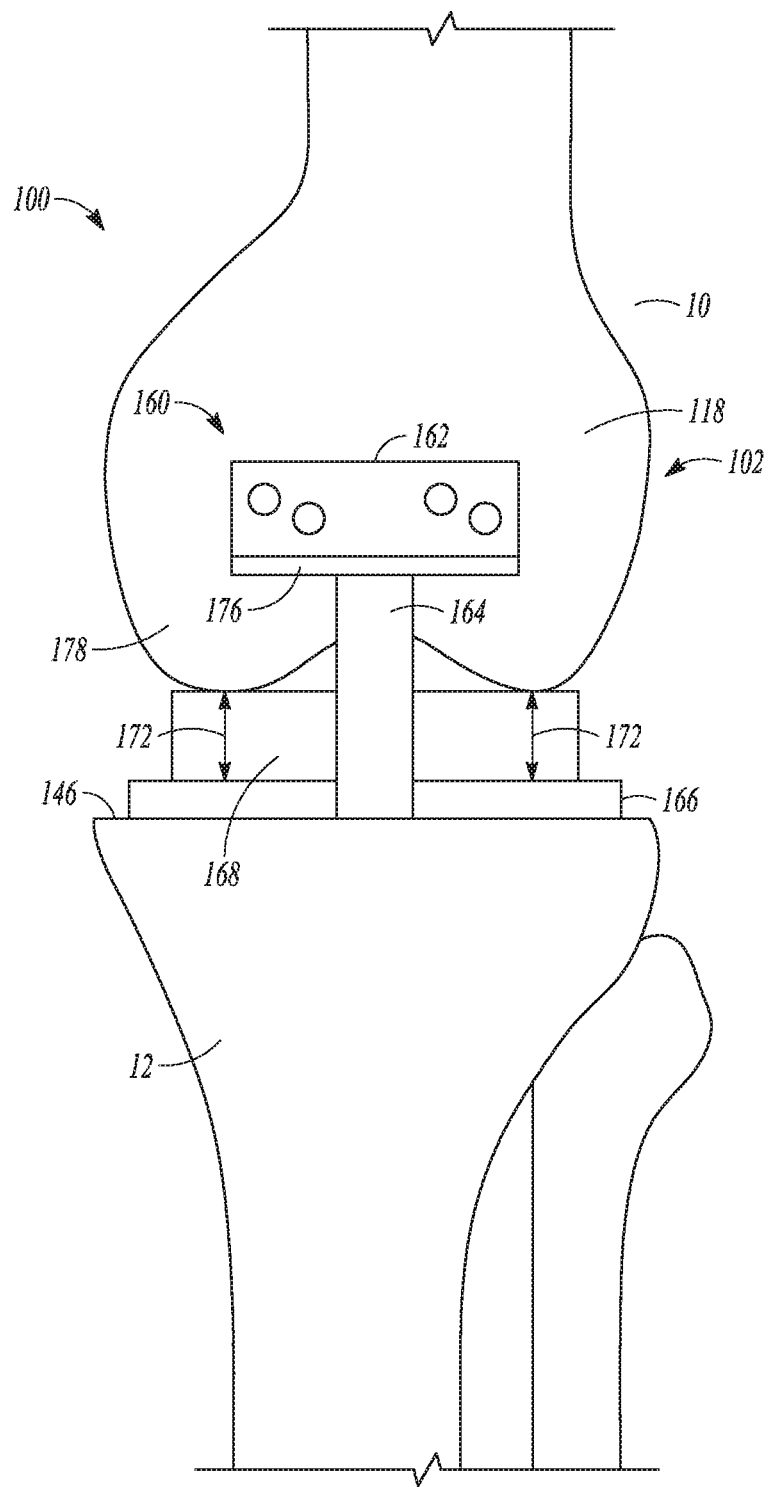
FIG. 6A is a plan view of the knee joint of the patient in the coronal plane having a third assembly positioned therein and adjacent thereto according to an example of the present application.
Figure 6B:
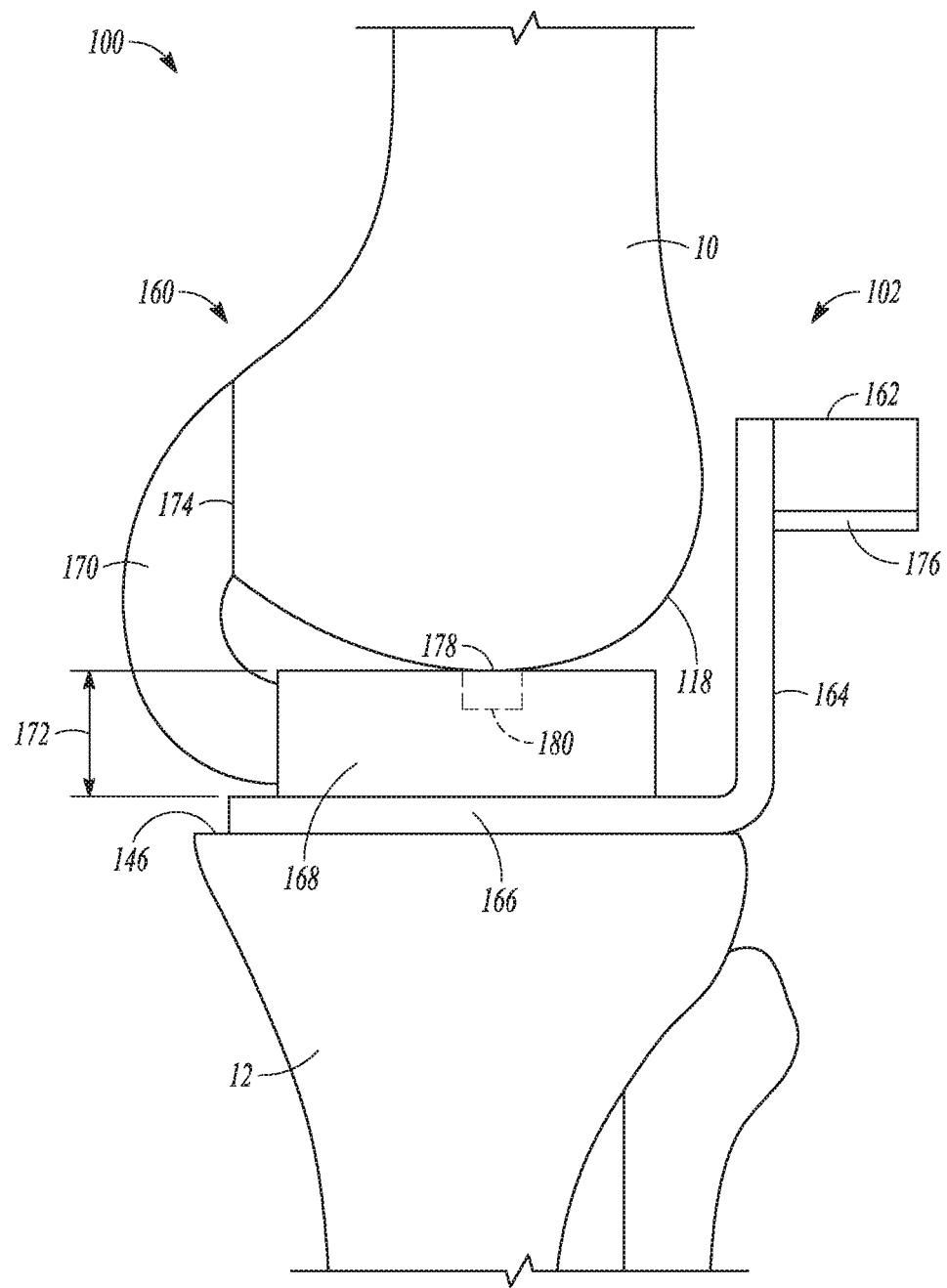
FIG. 6B is a plan view of the knee joint and the third assembly of FIG. 6A in a sagittal plane according to example of the present application.

The examples of FIGS. 5A-6B show a technique where the posterior and distal cuts are made and then the remaining femoral cuts can be performed using a finishing cut guide (e.g., a 4-in-1 cut guide). However, according to other examples the one or more aperture 149 can be used to drill holes to set femoral rotation but the posterior cut to the posterior condyle(s) may not be performed. Instead the technique can proceed to place the patient's knee joint 102 in extension as shown in FIGS. 6A and 6B, knee joint balancing to achieve an extension gap that substantially matches the flexion gap 148 can be performed as described below and desired drilling and resection of the distal portion of the condyle(s) of the femur using a third assembly 160 can also be performed as described below. After such techniques have been performed, the remaining resections to the femur 10 can be performed using the finishing cut guide (e.g., a 4-in-1 cut guide).

FIGS. 6A and 6B show an example of a third assembly 160 that can be part of the system 100. FIGS. 6A and 6B show an example where the posterior portion 116 (FIGS. 4A-5B) of the condyle 118 has been removed. However, according to other examples the posterior portion 116 may not be removed prior to use of the third assembly 160 described herein but can be removed subsequent to such use. FIGS. 6A and 6B also show an example where the third assembly 160 can be used with the knee joint 102 rotated from flexion as previously shown in FIGS. 4A to 5B to extension.

The third assembly 160 can include a femoral resection guide 162, a linkage 164, a tibial foot 166, one or more shims 168 and a member 170 (shown in FIG. 6B only). The femoral resection guide 162 can be connected by the linkage 164 to the tibial foot 166. According to some examples, the linkage 164 can be variable in length so as to be extensible and retractable. In other examples, the linkage 164 can have a fixed length. The tibial foot 166 can be configured to abut the resected proximal surface 146 of the tibia 12. In some examples, the tibial foot 166 can be configured to be secured or otherwise affixed to the resected proximal surface 146.

The one or more shims 168 can be inserted between the femur 10 and the tibia 12 contacting the tibial foot 166 and the femur 10. In some examples, the one or more shims 168 can be stackable upon one another. According to further examples, the one or more shims 168 can comprise a plurality of differently sized shims each having a different thickness from one another. The plurality of differently sized shims can be exchangeable for one another between the femur 10 and the tibia 12 until an extension gap 172 that substantially matches the flexion gap 148 (FIGS. 5A and 5B) has been achieved.

According some examples, the member 170 can be coupled to a resected posterior portion 174 of the condyle 118. The member 170 can be configured to simulate the posterior portion of the condyle 118. The member 170 can additionally contact and can support the one or more shims 168 upon insertion of the one or more shims 168 between the tibia 12 and femur 10.

The femoral resection guide 162 can be configured to define distal resection plane with a resection feature 176 along the femur 10 with the femur 10 in extension as illustrated in FIGS. 6A and 6B. The third assembly 160 can be configured to reference the resected proximal surface 146 of the tibia 12. More particularly, the tibial foot 166 and linkage 164 can be configured to reference and space the femoral resection guide 162 along the femur 10 a distance from the resected proximal surface 146 of the tibia 12. As previously discussed, the one or more shims 168 can be configured to be disposed between the tibia 12 and femur 10 to place the patient's knee joint 102 in tension to create the extension gap 172 that substantially matches the flexion gap 148 (FIGS. 5A and 5B).

Upon achieving the extension gap 172, and according to some examples, the femoral resection guide 162 can be used to aid in resection of a distal portion 178 of the femur 10 using the resection feature 176 as a guide.

According to some examples, the third assembly 160 can include one or more sensors 180 that can be configured to sense a pressure applied on the one or more shims 168 by one or both of the femur 10 and the tibia 12 (via the tibial foot 166). The sensed pressure can be used to determine the amount of resection/balancing desirable for the distal portion 178 by comparison with prior sensed pressure using the one or more sensors 121, for example.

Figure 7:
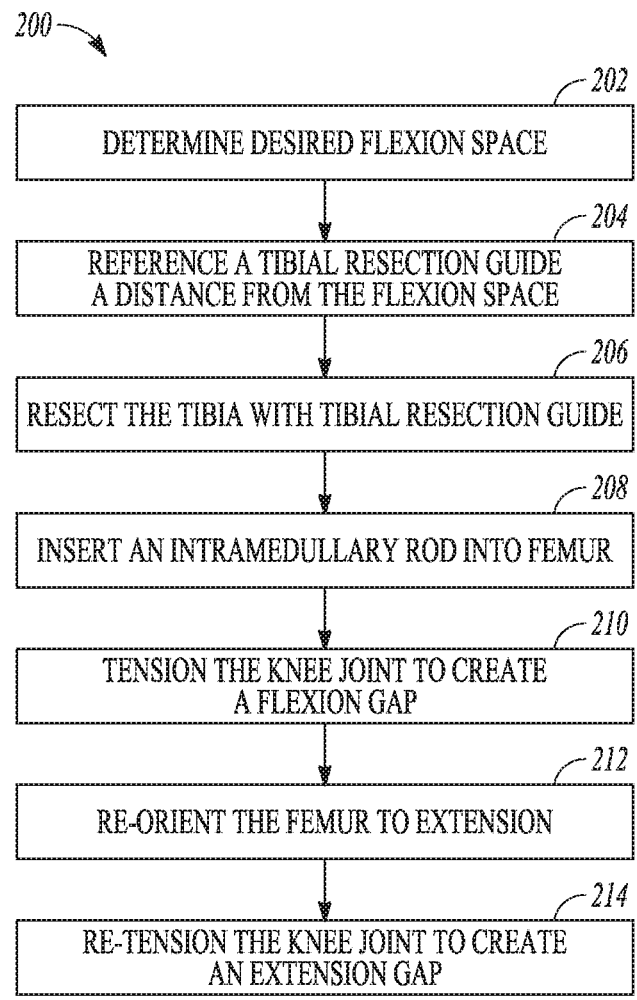
FIGS. 7 and 8 illustrated methods of performing a knee arthroplasty on the knee joint of the patient according to various examples.
Figure 8:
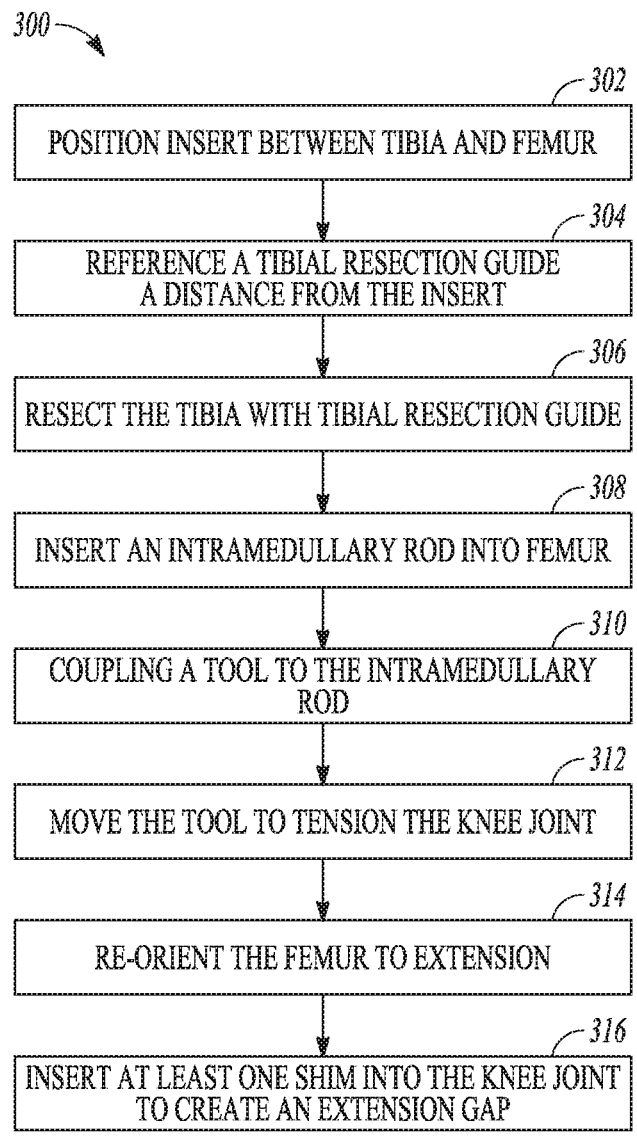

FIGS. 7 and 8 illustrate methods 200, 300 of performing a knee arthroplasty on a patient's knee joint according to various examples. In no particular order, the methods can check a flexion space, establish a resection of the tibia, drill and place an intramedullary rod, establish a flexion gap, size a femur, and match an extension space to the flexion space.

The method 200 of FIG. 7 can include determining 202 a desired flexion space between a tibia and a femur with the patient's knee joint oriented in flexion, referencing 204 a tibia resection guide along the tibia a distance from the desired flexion space, resecting 206 a proximal end portion of the tibia with the tibia resection guide, inserting 208 an intramedullary rod into the femur with the patient's knee joint in flexion, tensioning 210 the patient's knee joint to create a flexion gap by separating the tibia and the femur, sequent to tensioning the patient's knee joint, reorienting 212 the femur into extension relative to the tibia and re-tensioning 214 the patient's knee joint to create an extension gap that substantially matches the flexion gap.

According to further examples, the method 200 can further include any one or any combination of referencing a femoral resection guide relative to a resected proximal surface of the tibia with the femur in extension, sizing the femur sequent to reorienting the femur into the extension orientation and/or sensing a pressure between the tibia and the femur with the patient's knee joint oriented in both extension and flexion. The tensioning 210 of the patient's knee joint to create a flexion gap by separating the tibia and the femur can include coupling a tool to the intramedullary rod, the tool including a tibial component configured for placement against the tibia and a femoral component configured for placement against the femur, and moving the femoral component relative to the tibial component to place the patient's knee joint in tension to create a flexion gap by separating the tibia and the femur.

The method 300 of FIG. 8 can include positioning 302 an insert between a tibia and a femur with the patient's knee joint oriented in flexion, referencing 304 a tibia resection guide along the tibia a distance from the insert, resecting 306 a proximal end portion of the tibia with the tibia resection guide, inserting 308 an intramedullary rod into the femur with the patient's knee joint in flexion, coupling 310 a tool to the intramedullary rod, the tool including a tibial component configured for placement against the tibia and a femoral component configured for placement against the femur, moving 312 the femoral component relative to the tibial component to place the patient's knee joint in tension to create a flexion gap by separating the tibia and the femur, sequent to coupling the tool and moving the femoral component relative to the tibial component, reorienting 314 the femur into an extension orientation relative to the tibia and inserting 316 at least one shim between the tibia and femur to place the patient's knee joint in tension to create an extension gap that substantially matches the flexion gap.

According to further examples, the method 300 can further include any one or any combination of attaching a moveable stylus to the tool, the stylus having a head adapted for contact with an anterior surface of the femur at or adjacent an anterior cortex of the femur, repositioning the tool anterior/posterior to move the femoral component relative to a femoral condyle of the femur, adjusting flexion of the knee with the tool coupled to the intramedullary rod and the femur, providing one or more holes in the tool that define one or more drill paths into the femur, sensing a pressure applied on one or both of the insert and the at least one shim and/or contacting the at least one shim against a simulated posterior portion of a condyle of the femur. The method can include inserting a drill through at least one of the one or more holes in the tool, operating the drill to form one or more apertures in the femur, attaching a cut guide to the one or more apertures in the femur and performing a posterior femoral resection of the femur utilizing the cut guide.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various The claimed invention is:

1. A system for use in a knee arthroplasty of a patient's knee joint, the knee joint including a tibia and a femur, the system comprising:
a first assembly including an insert configured to be disposed between the tibia and the femur with the femur oriented in flexion, the insert configured to be contacted by a posterior portion of a condyle of the femur, the first assembly including a tibial resection guide configured to interface with a posterior portion of the tibia and configured to be disposed from the insert a predefined distance;
a second assembly including an intramedullary rod configured to insert into the femur with the femur in flexion and a tool configured to mount to the intramedullary rod, the tool including a tibial component configured for placement against the tibia and a femoral component configured for placement against the femur, the femoral component being moveably coupled to the tibial component to place the patient's knee joint in tension to create a flexion gap by separating the tibia and the femur; and
a third assembly including a femoral resection guide configured to define distal resection plane along the femur with the femur in extension, the third assembly configured to reference the femoral resection guide from a resected proximal surface of the tibia with the patient's knee joint in extension, the third assembly including one or more shims configured to be disposed between the tibia and femur to place the patient's knee joint in tension to create an extension gap that substantially matches the flexion gap.

2. The knee arthroplasty system of claim 1, wherein the tool has a slot extending one or both of generally anterior-posterior and proximal-distal and configured to receive the intramedullary rod therein.

3. The knee arthroplasty system of claim 1, further comprising a stylus configured to couple to the tool and reference an anterior cortex of the femur to determine a size of the femur.

4. The knee arthroplasty system of claim 1, wherein the tool defines one or more apertures configured to define a drill path into the distal femur.

5. The knee arthroplasty system of claim 1, wherein one or both of the insert and the one or more shims include one or more sensors configured to sense a pressure applied on the one or both of the insert and the one or more shims by one or both of the femur and tibia.

6. A method of performing a knee arthroplasty on a patient's knee joint, the method comprising:
determining a desired flexion space between a tibia and a femur with the patient's knee joint oriented in flexion;
referencing a tibia resection guide along the tibia a distance from the desired flexion space;
resecting a proximal end portion of the tibia with the tibia resection guide;
inserting an intramedullary rod into the femur with the patient's knee joint in flexion;
tensioning the patient's knee joint to create a flexion gap by separating the tibia and the femur;
sequent to tensioning the patient's knee joint, reorienting the femur into extension relative to the tibia; and
re-tensioning the patient's knee joint to create an extension gap that substantially matches the flexion gap.

7. The method of claim 6, further comprising referencing a femoral resection guide relative to a resected proximal surface of the tibia with the femur in extension.

8. The method of claim 6, further comprising sizing the femur sequent to reorienting the femur into the extension orientation.

9. The method of claim 6, further comprising sensing a pressure between the tibia and the femur with the patient's knee joint oriented in both extension and flexion.

10. The method of claim 6, wherein tensioning the patient's knee joint to create a flexion gap by separating the tibia and the femur comprises:
coupling a tool to the intramedullary rod, the tool including a tibial component configured for placement against the tibia and a femoral component configured for placement against the femur; and
moving the femoral component relative to the tibial component to place the patient's knee joint in tension to create a flexion gap by separating the tibia and the femur.

11. A method of performing a knee arthroplasty on a patient's knee joint, the method comprising:
positioning an insert between a tibia and a femur with the patient's knee joint oriented in flexion;
referencing a tibia resection guide along the tibia a distance from the insert;
resecting a proximal end portion of the tibia with the tibia resection guide;
inserting an intramedullary rod into the femur with the patient's knee joint in flexion;
coupling a tool to the intramedullary rod, the tool including a tibial component configured for placement against the tibia and a femoral component configured for placement against the femur;
moving the femoral component relative to the tibial component to place the patient's knee joint in tension to create a flexion gap by separating the tibia and the femur;
sequent to coupling the tool and moving the femoral component relative to the tibial component, reorienting the femur into an extension orientation relative to the tibia; and
inserting at least one shim between the tibia and femur to place the patient's knee joint in tension to create an extension gap that substantially matches the flexion gap.

12. The method of claim 11, further comprising attaching a moveable stylus to the tool, the stylus having a tip configured for contact with an anterior surface of the femur at or adjacent an anterior cortex of the femur.

13. The method of claim 11, further comprising repositioning the tool anterior/posterior to move the femoral component relative to a femoral condyle of the femur.

14. The method of claim 13, further comprising adjusting flexion of the knee with the tool coupled to the intramedullary rod and the femur.

15. The method of claim 11, further providing one or more holes in the tool that define one or more drill paths into the femur.

16. The method of claim 15, further comprising:
inserting a drill through at least one of the one or more holes in the tool;
operating the drill to form one or more apertures in the femur;

attaching a cut guide to the one or more apertures in the femur; and performing a posterior femoral resection of the femur utilizing the cut guide.

17. The method of claim 11, further comprising sensing a pressure applied on one or both of the insert and the at least one shim.

18. The method of claim 11, further comprising contacting the at least one shim against a simulated posterior portion of a condyle of the femur.

* * * * *